(12) United States Patent
Yu et al.

(10) Patent No.: US 6,376,750 B1
(45) Date of Patent: Apr. 23, 2002

(54) PLANT SEEDLING AND EMBRYO PROMOTER

(75) Inventors: Su-May Yu; Yu-Chan Chao, both of Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/575,574

(22) Filed: May 22, 2000

(51) Int. Cl.[7] ............... A01H 5/00; C12N 15/63; C07H 21/04
(52) U.S. Cl. ............ 800/287; 536/23.1; 536/23.6; 536/24.1; 435/6; 435/320.1; 435/410; 800/295
(58) Field of Search ............... 536/23.1, 23.6, 536/24.1; 435/6, 320.1, 410; 800/295, 287

(56) References Cited

U.S. PATENT DOCUMENTS 5,460,952 A  10/1995  Yu et al. ............ 435/69.1
5,677,474 A  10/1997  Rogers .............. 800/205
5,917,029 A   6/1999  Yu .................. 536/24.1

OTHER PUBLICATIONS

Wing et al, Database EST gb_gss5, Jan. 8, 1999, Accession No. AQ330339, p. 5.*
Lu et al., "Sugar Response . . . ," The Journal of Biological Chemistry, 273(17):10120–10131, 1998.
McElroy et al., "Characterization of . . . ," Plant Molecular Biology, 15:257–268, 1990.
Zhang et al., "Analysis of Rice . . . ," The Plant Cell, 3:1155–1165, 1991.

* cited by examiner

*Primary Examiner*—Sean McGarry
(74) *Attorney, Agent, or Firm*—Fish & Richardson P.C.

(57) ABSTRACT

The invention relates to the promoter of a rice glycine-rich RNA binding protein gene and its use for expression of heterologous proteins in plant tissues, including tissues of the plant embryo and seedling.

26 Claims, No Drawings

```
                              SEQUENCE LISTING

<160> NUMBER OF SEQ ID NOS:  10

<210> SEQ ID NO 1
<211> LENGTH: 180
<212> TYPE: DNA
<213> ORGANISM: Oryza sativa

<400> SEQUENCE: 1
tgtggtgggc cgcggcggcc cataaaagaa atatctaggc ggcccatgta g cgccagaaa      60 atatcttctc ccccgcctcg ggatccttat cctccgcctc gcgcggggtg c cgtccgatc     120 agatcaggac ggccgcgtgg ggctataaaa ggagggggg tagggcaagc a tgtcctcct     180

<210> SEQ ID NO 2
<211> LENGTH: 500
<212> TYPE: DNA
<213> ORGANISM: Oryza sativa

<400> SEQUENCE: 2
aaaaaattaa aaagccagtt acgtataaag tattaatcat attttatcat a taacaacaa     60 tgaaaatact aattataaaa atttttcata taagacggac agttaaacgt t ggacacgaa    120 aatctaggat ttattttttt ttatagaggg agtacgaggt aaaaatcgtc c tcagcgcct    180 tcagaaaaaa aaaggacaaa aatcctcagc gccaaccgac tccgctccac a gaccacagc    240 cgcccaagtg tgcgaggaca acggcggcgg cggcggcggc taggttttg c tgcacccga    300 cgccaccgcc caccagcgag tgtggtgggc cgcggcggcc cataaaagaa a tatctaggc    360 ggcccatgta gcgccagaaa atatcttctc ccccgcctcg ggatccttat c ctccgcctc    420 gcgcggggtg ccgtccgatc agatcaggac ggccgcgtgg ggctataaaa g aggggggg    480 tagggcaagc atgtcctcct                                                 500

<210> SEQ ID NO 3
<211> LENGTH: 3572
<212> TYPE: DNA
<213> ORGANISM: Oryza sativa

<400> SEQUENCE: 3
tagcttctaa taattgttag taggtatcaa tagattgttt aatttaactg g ccatggaaa    60 gaatggtatt ggcatcaatg gcatgaccgt ttctataaaa cccttcttat t gatcaatgc   120 atgatatctt taattaaatc cccttccct ttttctcttc taaggtgatg t ttggaacca   180 gatacttaac tttagtctat atatttagac actaatttag agtattaaat a tagactact   240 tacaaaacta attacataaa tgaaagctaa tttgcgagat aaatttttta a gcctaatta   300 atctataatt agagaatttt tactgtagca tcatataggc atatcatgga t taattaggc   360 tcaatagatt tgtctcgcga attagtccga gattatggat gagttttatt g atagtctac   420 gtttaatatt tataattagt gtccaaacat cccatgtaat agggacttaa a agttttagt   480 cccatctaaa cagggtctaa gtccttctaa atctgttact catataactg t ctaactgag   540 ataaagttta aggttgtcat atcatatcat cgtcacgtta tatatatgat c cctgcactt   600 ctcttttat agaatggacg agactctttt ttctgtatat gtagcggtct t gtactcttg   660 ttagtaccat tttgcgtccc attttgacga gacgactggc gtgccatttt g cgtcctggt   720
```

-continued

| | |
|---|---|
| tcattacagt ctaatttggt gacaaacaaa caaggaacaa ataggtccca t ggtctagcg | 780 |
| gttaggacat tggactctga atccagtaac ccgagttcaa atctcggtgg g accttaatt | 840 |
| ttctcggttt tattttctgc ctgagcttat tgtcctcctc ctgatttttt g ttgttgtct | 900 |
| attttctctg ccggaaaaat gtatcaaact cgtcgattct actcgtttga g agcttactg | 960 |
| tgatattgtc cttctcctga agtttctatt ttttactctc tctgttatga a aattttcat | 1020 |
| gctagaatga tttacattgt gaaatggaga gagaactcgt tgtgcttat t tatccttcc | 1080 |
| cctgattttt ttccacacca aaacatatat tgtgataatt gagtatgcta c cgtctgac | 1140 |
| gtactacgag tttactccct ccgtcccaaa aaagacaaa ccctgagttt t catgtccaa | 1200 |
| tgtttgatca tattatttga aaaaattatg aaaaaattaa aaagccagtt a cgtataaag | 1260 |
| tattaatcat atttatcat ataacaacaa tgaaaatact aattataaaa a tttttcata | 1320 |
| taagacggac agttaaacgt tggacacgaa atctaggat ttatttttttt t tatagaggg | 1380 |
| agtacgaggt aaaaatcgtc ctcagcgcct tcagaaaaaa aaaggacaaa a atcctcagc | 1440 |
| gccaaccgac tccgctccac agaccacagc cgcccaagtg tgcgaggaca a cggcggcgg | 1500 |
| cggcggcggc taggttttttg ctgcacccga cgccaccgcc caccagcgag t gtggtgggc | 1560 |
| cgcggcggcc cataaaagaa atatctaggc ggcccatgta cgccagaaa a tatcttctc | 1620 |
| ccccgcctcg ggatccttat cctccgcctc gcgcgggggtg ccgtccgatc a gatcaggac | 1680 |
| ggccgcgtgg ggctataaaa ggagggggggg tagggcaagc atgtcctcct c gtgctctct | 1740 |
| ttgaggtggg ttggcttctc ctcccccctct ttaccttttc ctcctcggtt c ggttccgtg | 1800 |
| gttcgtctag ggtttagtgg gttgagatgg cggcgccgga tgtcgagtac c gctgcttcg | 1860 |
| tcggcggcct cgcctgggcc accgacgacc gctccctcga ggccgccttc t ccacctacg | 1920 |
| gcgagatcct cgactccaag gttcgccctc gctctcctac gccgtgtctt g tgatgggtt | 1980 |
| tttttttgggt ggtttctcgt gttggctgga tctgtgttga atttgtttgg g tttttttgt | 2040 |
| tggtttgctc ggatctgtga tcctgggggg ttttgctcgt gctgttctga t ctcgttggt | 2100 |
| gccagatctg tgtggagggg ttgatttggt ggttttttttg ggtggatctg a tggggattt | 2160 |
| gtgtgttttt gttttggttg tttgcagatc atcaacgaca gggagacggg g aggtcacgt | 2220 |
| gggtttggct tcgtcacctt ctcctccgag cagtcgatgc gcgacgccat c gagggcatg | 2280 |
| aacggcaagg agctcgacgg ccgcaacatc accgtcaatg aggcccagtc c cgccgctcc | 2340 |
| ggcggcggag gcgggggcta cggcggcggc ggtggcggct acggcggcgg t cgtggaggc | 2400 |
| ggcggctacg gaggaggtgg cggcggcggc tacggcgcc gtgagggcgg c tacggtggc | 2460 |
| ggcggcggct acgcggcgg ccgtggcggc ggcggcggcg gctacggtgg c agccgtggc | 2520 |
| ggcggctacg gcggcgactc cggcgggaac tggaggaact gattggtggg g cccatcgtg | 2580 |
| gccagttatc cttagctatc cgtgtcagaa tcatcttatc atcgaatcga g tcgttatcg | 2640 |
| tgtccagtgg ctctctcgag tcgagaagcc ctctatccat ccatccagtg t taggtgttc | 2700 |
| ttgctccgtg atcttaccat gaattgagtt cgctttggtt atggtgtttg a actgcttgt | 2760 |
| tgctatctat cggaatgaaa tgaaatagaa acaaggaga aaaaaaagag t tcgaaagtt | 2820 |
| ttgttcgcat accatatatt tccttccggt gcgcgctgtt tattcctcgc t cagcagcaa | 2880 |
| gattgtttga tcgatattgc agcaagcaat tcacaataaa tatattgcta c actcctact | 2940 |
| tcaaactaca ctggtggtcg gtgattttca atagcatgaa ccttaattga a catctgtgt | 3000 |
| agcttacatc tccttcgaaa gctgcaatgc ttgagaactt ggaaagaaat t cttgtgatg | 3060 |
| gcagaagcta ttcactgtcc ttcgctgcat ttacagtcca tacagacaca g catttccat | 3120 |

-continued

```
tttgcacaag atagagaaca acaatcagcc ttttaggtca atcccaagtg t gcatcttac      3180 tgattgtcga atatgtgcta agaacctgca agagagtgag gattttttatc a ttgattgat   3240 tgtcgaatat atgctaagaa ccttcaagag agtgaggatt tttatcattg a tggagcttt   3300 gtttctgtaa tccaagattt gggaaacagt ttatccatgt tagggaaatg a tttatgcaa   3360 acaatatttt ggagcaaaag ttagatagta gtatatgtct gccgacgacc t caacccaaa   3420 atattgtttt gaggaactct tggattacag aacaaaatac tgattccaaa c aatcatact   3480 tttttaacac aaccatcaca ttggagattt caaaacagca gagatgatag g atctactct   3540 ttccatgtct tcatccaaac ttaattaagc tt                                   3572
```

<210> SEQ ID NO 4
<211> LENGTH: 162
<212> TYPE: PRT
<213> ORGANISM: Oryza sativa

<400> SEQUENCE: 4

```
Met Ala Ala Pro Asp Val Glu Tyr Arg Cys P he Val Gly Gly Leu Ala
 1               5                  10                  15

Trp Ala Thr Asp Asp Arg Ser Leu Glu Ala A la Phe Ser Thr Tyr Gly
            20                  25                  30

Glu Ile Leu Asp Ser Lys Ile Ile Asn Asp A rg Glu Thr Gly Arg Ser
        35                  40                  45

Arg Gly Phe Gly Phe Val Thr Glu Ser Ser G lu Gln Ser Met Arg Asp
    50                  55                  60

Ala Ile Glu Gly Met Asn Gly Lys Glu Leu A sp Gly Arg Asn Ile Thr
65                  70                  75                  80

Val Asn Glu Ala Gln Ser Arg Arg Ser Gly G ly Gly Gly Gly Gly Tyr
                85                  90                  95

Gly Gly Gly Gly Gly Gly Tyr Gly Gly Gly A rg Gly Gly Gly Gly Tyr
            100                 105                 110

Gly Gly Gly Gly Gly Gly Tyr Gly Arg A rg Glu Gly Gly Tyr Gly
        115                 120                 125

Gly Gly Gly Tyr Gly Gly Arg Gly G ly Gly Gly Gly Tyr
    130                 135                 140

Gly Gly Ser Arg Gly Gly Gly Tyr Gly Gly A sp Ser Gly Gly Asn Trp
145                 150                 155                 160

Arg Asn
```

<210> SEQ ID NO 5
<211> LENGTH: 1730
<212> TYPE: DNA
<213> ORGANISM: Oryza sativa

<400> SEQUENCE: 5

```
tagcttctaa taattgttag taggtatcaa tagattgttt aatttaactg g ccatggaaa     60 gaatggtatt ggcatcaatg gcatgaccgt ttctataaaa ccccttcttat t gatcaatgc  120 atgatatctt taattaaatc ccctttccct ttttctcttc taaggtgatg t ttggaacca  180 gatacttaac tttagtctat atatttagac actaatttag agtattaaat a tagactact  240 tacaaaacta attacataaa tgaaagctaa tttgcgagat aaatttttta a gcctaatta  300 atctataatt agagaatttt tactgtagca tcatataggc atatcatgga t taattaggc  360 tcaatagatt tgtctcgcga attagtccga gattatggat gagttttatt g atagtctac  420 gtttaatatt tataattagt gtccaaacat cccatgtaat agggacttaa a gttttagt   480
```

-continued

```
cccatctaaa cagggtctaa gtccttctaa atctgttact catataactg t ctaactgag     540 ataaagttta aggttgtcat atcatatcat cgtcacgtta tatatatgat c cctgcactt     600 ctctttttat agaatggacg agactctttt ttctgtatat gtagcggtct t gtactcttg     660 ttagtaccat tttgcgtccc attttgacga gacgactggc gtgccatttt g cgtcctggt     720 tcattacagt ctaatttggt gacaaacaaa caaggaacaa ataggtccca t ggtctagcg     780 gttaggacat tggactctga atccagtaac ccgagttcaa atctcggtgg g accttaatt     840 ttctcggttt tattttctgc ctgagcttat tgtcctcctc ctgatttttt g ttgttgtct     900 attttctctg ccggaaaaat gtatcaaact cgtcgattct actcgtttga g agcttactg     960 tgatattgtc cttctcctga agtttctatt ttttactctc tctgttatga a aattttcat    1020 gctagaatga tttacattgt gaaatggaga gagaactcgt ttgtgcttat t tatccttcc    1080 cctgattttt ttccacacca aaacatatat tgtgataatt gagtatgcta c cgtctgac    1140 gtactacgag tttactccct ccgtcccaaa aaaagacaaa ccctgagttt t catgtccaa    1200 tgtttgatca tattatttga aaaaattatg aaaaaattaa aaagccagtt a cgtataaag    1260 tattaatcat attttatcat ataacaacaa tgaaaatact aattataaaa t tttttcata    1320 taagacggac agttaaacgt tggacacgaa aatctaggat ttattttttt t tatagaggg    1380 agtacgaggt aaaaatcgtc ctcagcgcct tcagaaaaaa aaaggacaaa a atcctcagc    1440 gccaaccgac tccgctccac agaccacagc cgcccaagtg tgcgaggaca a cggcggcgg    1500 cggcggcggc taggttttg ctgcacccga cgccaccgcc caccagcgag t gtggtgggc    1560 cgcggcggcc cataaaagaa atatctaggc ggcccatgta gcgccagaaa a tatcttctc    1620 ccccgcctcg ggatccttat cctccgcctc gcgcggggtg ccgtccgatc a gatcaggac    1680 ggccgcgtgg ggctataaaa ggagggggggg tagggcaagc atgtcctcct              1730
```

```
<210> SEQ ID NO 6
<211> LENGTH: 100
<212> TYPE: DNA
<213> ORGANISM: Oryza sativa

<400> SEQUENCE: 6
gccaccgccc accagcgagt gtggtgggcc gcggcggccc ataaaagaaa t atctaggcg     60 gcccatgtag cgccagaaaa tatcttctcc cccgcctcgg                           100

<210> SEQ ID NO 7
<211> LENGTH: 100
<212> TYPE: DNA
<213> ORGANISM: Oryza sativa

<400> SEQUENCE: 7
ggatccttat cctccgcctc gcgcggggtg ccgtccgatc agatcaggac g gccgcgtgg     60 ggctataaaa ggagggggggg tagggcaagc atgtcctcct                          100

<210> SEQ ID NO 8
<211> LENGTH: 17
<212> TYPE: DNA
<213> ORGANISM: Artificial Sequence
<220> FEATURE:
<223> OTHER INFORMATION: Synthetically generated p rimer

<400> SEQUENCE: 8
ctcaacccac taaaccc                                                    17
```

```
<210> SEQ ID NO 9
<211> LENGTH: 27
<212> TYPE: DNA
<213> ORGANISM: Artificial Sequence
<220> FEATURE:
<223> OTHER INFORMATION: Synthetically generated p rimer

<400> SEQUENCE: 9
gatatctgca gctcaaccca ctaaacc                                              27

<210> SEQ ID NO 10
<211> LENGTH: 17
<212> TYPE: DNA
<213> ORGANISM: Artificial Sequence
<220> FEATURE:
<223> OTHER INFORMATION: Synthetically generated p rimer

<400> SEQUENCE: 10
cgtgctctct ttgaggt                                                         17
```

PLANT SEEDLING AND EMBRYO PROMOTER

BACKGROUND OF THE INVENTION

The use of transgenic plants for the production of pharmaceutical proteins and industrial enzymes has been proposed. In general, expression of recombinant proteins relies on stable integration of a heterologous gene into a host plant genome using, e.g., Agrobacterium-mediated. transformation or particle bombardment. In terms of cost, production of commercially valuable proteins using crops in the field is more competitive than other biological production systems (such as yeast, bacteria, or mammalian cell cultures) which require complex and high-maintenance bioreactors. Further, protein production in plant can be easily scaled-up to produce large quantities.

SUMMARY OF THE INVENTION

The invention is based on the discovery of a new promoter derived from a rice gene encoding for a glycine-rich RNA binding protein (designated OsGRP-A1). The OsGRP-A1 promoter can be used to express proteins in a plant and its tissues and organs, especially in the seedling, embryo, or sprout tissues. The sequence of OsGRP-A1 gene is shown below:

```
-1730 tagcttctaataattgttagtaggtatcaatagattgtttaatttaactg
-1680 gccatggaaagaatggtattggcatcaatggcatgaccgtttctataaaaccttcttat
-1620 tgatcaatgcatgatatctttaattaaatcccctttccctttttctcttctaaggtgatg
-1560 tttggaaccagatacttaactttagtctatatatttagacactaatttagagtattaaat
-1500 atagactacttacaaaactaattacataaatgaaagctaatttgcgagataaatttttta
-1440 agcctaattaatctataattagagaattttttactgtagcatcatataggcatatcatgga
-1380 ttaattaggctcaatagatttgtctcgcgaattagtccgagattatggatgagttttatt -1320 gatagtctacgtttaatatttataattagtgtccaaacatcccatgtaatagggacttaa
-1260 aagttttagtcccatctaaacagggtctaagtccttctaaatctgttactcatataactg
-1200 tctaactgagataaagtttaaggttgtcatatcatatcatcgtcacgttatatatatgat
-1140 ccctgcacttctcttttatagaatggacgagactcttttttctgtatatgtagcggtct
-1080 tgtactcttgttagtaccattttgcgtcccattttgacgagacgactggcgtgccatttt
-1020 gcgtcctggttcattacagtctaatttggtgacaaacaaacaaggaacaaataggtccca
 -960 tggtctagcggttaggacattggactctgaatccagtaacccgagttcaaatctcggtgg
 -900 gaccttaattttctcggttttattttctgcctgagcttattgtcctcctcctgattttt
 -840 gttgttgtctattttctctgccggaaaaatgtatcaaactcgtcgattctactcgtttga
 -780 gagcttactgtgatattgtccttctcctgaagtttctattttttactctctctgttatga
 -720 aaattttcatgctagaatgatttacattgtgaaatggagagagaactcgtttgtgcttat
 -660 ttatccttcccctgatttttttccacaccaaaacatatattgtgatggttgagtatgcta
 -600 cgcgtctgacgtactacgagtttactccctccgtcccaaaaaaagacaaaccctgagttt
 -540 tcatgtccaatgtttgatcatattatttgaaaaaattatgaaaaaattaaaaagccagtt
 -480 acgtataaagtattaatcatattttatcatataacaacaatgaaaatactaattataaaa
 -420 atttttcatataagacggacagttaaacgttggacacgaaaatctaggatttatttttt
 -360 ttatagagggagtacgaggtaaaaatcgtcctcagcgccttcagaaaaaaaaaggacaaa
 -300 aatcctcagcgccaaccgactccgctccacagaccacagccgcccaagtgtgcgaggaca
 -240 acggcggcggcggcgcggctaggttttttgctgcacccgacgccaccgcccaccagcgag
 -180 tgtggtgggccgcggcggcccataaagaaatatctaggcggcccatgtagcgccagaaa
 -120 atatcttctcccccgcctcgggatccttatcctccgcctcgcgcggggtgccgtccgatc
  -60 agatcaggacggccgcgtggggctataaaggagggggggtagggcaagcatgtcctcct
    1 CGTGCTCTCTTTGAGGTGGGTTGGCTTCTCCTCCCCCTCTTTACCTTTTCCTCCTCGGTT
```

-continued
```
  61 CGGTTCCGTGGTTCGTCTAGGGTTTAGTGGGTTGAGATGGCGGCGCCGGATGTCGAGTAC
                                   M  A  A  P  D  V  E' Y 121 CGCTGCTTCGTCGGCGGCCTCGCCTGGGCCACCGACGACCGCTCCCTCGAGGCCGCCTTC
      R  C  F  V  G  G  L  A  W  A  T  D  D  R  S  L  E  A  A  F 181 TCCACCTACGGCGAGATCCTCGACTCCAAGgttcgccctcgctctcctacgccgtgtctt
      S  T  Y  G  E  I  L  D  S  K 241 gtgatgggttttttttgggtggtttctcgtgttggctggatctgtgttgaatttgtttgg 301 gttttttttgttggtttgctcggatctgtgatcctggggggttttgctcgtgctgttctga 361 tctcgttggtgccagatctgtgtggaggggttgatttggtggttttttttgggtggatctg 421 atggggatttgtgtgtttttgttttggttgtttgcagATCATCAACGACAGGGAGACGGG
                                            I  I  N  D  R  E  T  G 481 GAGGTCACGTGGGTTTGGCTTCGTCACCTTCTCCTCCGAGCAGTCGATGCGCGACGCCAT
      R  S  R  G  F  G  F  V  T  E  S  S  E  Q  S  M  R  D  A  I 541 CGAGGGCATGAACGGCAAGGAGCTCGACGGCCGCAACATCACCGTCAATGAGCCCAGTC
      E  G  M  N  G  K  E  L  D  G  R  N  I  T  V  N  E  A  Q  S 601 CCGCCGCTCCGGCGGCGGAGGCGGGGCTACGGCGGCGGCGGTGGCGGCTACGCGGCGG
      R  R  S  G  G  G  G  G  Y  G  G  G  G  G  Y  G  G 661 TCGTGGAGGCGGCGGCTACGGAGGAGGTGGQGGCGGCGGCTACGGGCGCCGTGAGGGCGG
      R  G  G  G  Y  G  G  G  G  G  G  Y  G  R  R  E  G  G 721 CTACGGTGGCGGCGGCGGCTACGGCGGCGCCGTGGCGGCGGCGGCGGCTACGGTGG
      Y  G  G  G  G  Y  G  G  G  R  G  G  G  G  G  Y  G  G 781 CAGCCGTGGCGGCGGCTACGGCGGCGACTCCGGCGGGAACTGGAGGAACTGATTGGTGGG
      S  R  G  G  G  Y  G  G  D  S  G  G  N  W  R  N  *  (SEQ ID NO:4)

841 GCCCATCGTGGCCAGTTATCCTTAGCTATCCGTGTCAGAATCATCTTATCATCGAATCGA

901 GTCGTTATCGTGTCCAGTGGCTCTCTCGAGTCGAGAAGCCCTCTATCCATCCATCCAGTG

961 TTAGGTGTTCTTGCTCGGTGATCTTACCATGAATTGAGTTCGCTTTGGTTATGGTGTTTG

1021 AACTGCTTGTTGCTATCTATCGGAATGAAATGAAATAGAAAACAAGGAGAAAAAAAAGAG

1081 TTCGAAAGTTTTGTTCGCATACCATATATTTCCTTCCGGTGCGCGCTGTTTATTCCTCGC

1141 TCAGCAGCAAGATTGTTTGATCGATATTGCAGCAAGCAATTCACAATAAATATATTGCTA

1201 CACTCCTACTTCAAACTACACTGGTGGTCGGTGATTTTCAATAGCATGAACCTTAATTGA

1261 ACATCTGTGTAGCTTACATCTCCTTCGAAAGCTGCAATGCTTGAGAACTTGGAAAGAAAT 1321 tcttgtgatggcagaagctattcactgtccttcgctgcatttacagtccatacagacaca 1381 gcatttccattttgcacaagatagagaacaacaatcagccttttaggtcaatcccaagtg 1441 tgcatcttactgattgtcgaatatgtgctaagaacctgcaagagagtgaggattttatc 1501 attgattgattgtcgaatatatgctaagaaccttcaagagagtgaggattttatcattg 1561 atggagctttgtttctgtaatccaagatttgggaaacagtttatccatgttagggaaatg 1621 atttatgcaaacaatattttggagcaaaagttagatagtagtatatgtctgccgacgacc 1681 tcaacccaaaatattgttttgaggaactcttggattacagaacaaaatactgattccaaa 1741 caatcatactttttttaacacaaccatcacattggagatttcaaaacagcagagatgatag 1801 gatctactctttccatgtcttcatccaaacttaattaagctt (SEQ ID NO:3)
```

As indicated above, the complete nucleotide sequence of OsGRP-A1 is designated SEQ ID NO:3, while the complete amino acid sequence of the protein encoded by OsGRP-A1 is designated SEQ ID NO:4. The upper case nucleotides represent the cDNA sequence, while the lower case nucleotides represent the genomic sequences flanking the cDNA and in the intron. Nucleotide numberings are relative to the transcription start site. The putative TATA box is underlined. The OsGRP-A1 protein contains two consensus RNA binding domains (amino acids 10–15 and 49–56 of SEQ ID NO:4), which are shown in italics. A minimal promoter sequence from −180 to −1 is designated SEQ ID NO:1 (bolded sequence), a larger promoter sequence from −500 to −1 is designated SEQ ID NO:2, and the promoter-containing genomic sequence upstream of the transcriptional start site (from −1730 to −1) is designated SEQ ID NO:5.

This new promoter was shown to direct expression of a heterologous protein in transgenic rice seeds and embryos during germination and in cultured rice suspension cells. Consequently, the promoter can be used to regulate and direct expression of a heterologous protein or RNA (e.g., an antisense RNA) in transgenic plants, organs thereof, or in plant cells.

Accordingly, the invention features an isolated nucleic acid including SEQ ID NO:1 (e.g., SEQ ID NO:2), a promoter that hybridizes under stringent conditions to SEQ ID NO:1, or a promoter that is at least 50% (e.g., at least 60, 70, 80, 90, or 95%) identical to SEQ ID NO:1. The nucleic acid of the invention can further include a heterologous sequence to which a promoter containing SEQ ID NO:1 is operably linked, i.e., the promoter directs transcription of the heterologous sequence. The invention also includes vectors and transformed cells harboring a nucleic acid of the invention, as well as transgenic plants (e.g., a transgenic sprout or seedling) whose genomic DNA contains a nucleic acid of the invention. The transgenic plant can be a monocot (e.g., rice) or dicot. The invention further features a method of producing a transgenic plant or organ of a plant (e.g., a seed) by stably introducing a nucleic acid of the invention into a plant cell, and culturing the plant cell under conditions sufficient for the plant cell to form a plant or organ of a plant.

The invention also features nucleic acids containing SEQ ID NO:5 or a fragment thereof. These fragments are at least 6 nucleotides in length, e.g., at least 10, 15, 20, 50, 100, or 500 nucleotides in length.

An "isolated nucleic acid" is a nucleic acid which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are mixtures of DNA molecules, vectors, or clones as they occur in a DNA library such as a cDNA or genomic DNA library. Also excluded are RNA molecules that consist of naturally occurring sequences (e.g., naturally occurring mRNA), except where the RNA is in a purified state such that it is at least 90% free of other naturally occurring RNA species. Thus, a naturally occurring mRNA in a whole mRNA preparation prepared from a cell would not be an "isolated nucleic acid," but a single mRNA species purified to 90% homogeneity from that whole mRNA preparation would be.

As used herein, "percent identity" of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410. 1990). BLAST nucleotide searches are performed with the NBLAST program, score= 100, wordlength=12 to obtain nucleotide sequences homologous to a nucleic; acid molecules of the invention. To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nhn.nih.gov.

By "hybridizes under stringent conditions" is meant specific and non-covalent equilibrium binding by base-pairing to an immobilized reference nucleic acid in a hybridization solution containing 0.2×SSC (1.75 g/l NaCl, 0.88 g/l $Na_3$citrate.$2H_2O$; pH 7.0) and 0.1% (w/v) sodium dodecylsulfate at 68° C. Washings, if any are required to achieve equilibrium, are carried out with the hybridization solution.

A "heterologous sequence" is a nucleotide sequence that is not naturally operably linked to the OsGRP-A1 promoter in a naturally occurring organism.

A "promoter" is a nucleotide sequence that is capable of directing transcription in at least one context, e.g., when it is operably linked to a heterologous sequence in a plasmid within a plant cell. In other words, a promoter can exist without downstream sequences to transcribe, so long as the promoter sequence can direct transcription when placed upstream of a heterologous sequence in a different context.

The sprout or seedling can be derived from monocots or dicots. As used herein, the term "sprout" means a young shoot, including the cotyledon (as in dicots), scutellum (as in monocots), hypocotyl (the shoot below the cotyledon, as in bean), epicotyl (the shoot above the cotyledon, as in pea), coleoptile (as in cereal grains), and young root (radicle) grown from embryo of germinating seed. Germination begins with water uptake by the seed (imbibition) and ends with the start of elongation by the embryonic axis, usually the radicle. Therefore, germination does not include seedling growth, which commences when germination terminates. For germination to be completed, the radicle must expand and penetrate the surrounding structures. As used herein, the term "seedling" means the juvenile plant grown from a sprout or a germinating seed, as defined in de Vogel, "The Seedling," In: *Seedlings of Dicotyledons*, Centre for Agricultural Publishing and Documentation, Wageningen, Netherlands, pp 9–25, 1983.

The promoter sequence of the invention can be introduced into a variety of plant expression vectors for expressing exogenous proteins in plant cells, transgenic plants, and seeds or embryos thereof. In addition, the isolated nucleic acids of the invention can be used as probes to isolate other promoters and/or genes that have the same expression pattern as e described herein (e.g., high level expression in seedling or embryo tissue). For example, nucleotides 1530 to 1630 (SEQ ID NO:6) or 1630 to 1730 (SEQ ID NO:7) of SEQ ID NO:1 can be used to screen genomic DNA libraries for genes that are regulated similarly to OsGRP-A1. Further, the methods of the invention can be used to produce transgenic plants or organs having specialized properties (e.g., longer shelf-life) as a consequence of expressing a heterologous RNA (e.g., a mRNA encoding an anti-ageing protein or an anti-sense RNA that inhibits expression of a senescence-associated gene) in a tissue or organ of a plant.

Further, nucleic acids containing SEQ ID NO:5 or fragments thereof can be used as a promoter (e.g., SEQ ID .NO:1) or as a probe for isolating gene promoters having the expression pattern for OsGRP-A1, as described herein.

Other features or advantages of the present invention will be apparent from the following detailed description, and also from the claims.

DETAILED DESCRIPTION

The invention relates to a new promoter for expressing heterologous proteins in plant cells and plants (including seeds, sprouts, and seedlings of the plant). Contemplated within the scope of the invention are vectors, transformed cells (produced by genomic integration or extrachromosomal replication of a plasmid), and transgenic plants containing a promoter of the invention operably linked to a heterologous sequence. The heterologous sequence can encode an antisense RNA that blocks the expression of a gene, e.g., responsible for senescence in a tissue of the plant.

Vectors, such as expression vectors, can be used to propagate the promoter sequence in bacteria. In this context, it is noted that the promoter sequence can be separated from any heterologous sequence during the propagation step. Vectors can be viral vectors in which the nucleic acids of the invention are ligated into viral genomes. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, expression vectors are capable of directing the expression of genes to which they are operatively linked. The invention is intended to include expression vectors and viral vectors.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, particle bombardment, or electroporation.

Genes having a promoter of the invention can be expressed in transgenic plant cells. In order to produce transgenic plants, vectors containing a gene including a promoter of the invention are inserted into the plant genome. These recombinant vectors are capable of stable integration into the plant genome. One variable in making a transgenic plant is the choice of a selectable marker gene. A selectable marker gene is used to identify transformed cells against a high background of untransformed cells. Such selectable marker genes include the aminoglycoside phosphotransferase gene of transposon Tn5 (Aph II), which encodes resistance to the antibiotics kanamycin, neomycin, and G418, as well as those genes which encode for resistance or tolerance to glyphosate, hygromycin, methotrexate, phosphinothricin, imidazolinones, sulfonylureas, and triazolophyrimidine herbicides, such as chlorosulfuron, bromoxynil, dalapon and the like. In addition to a selectable marker gene, it may be desirable to use a reporter gene. In some instances a reporter gene may be used with a selectable marker. Reporter genes allow the detection of a transformed cell and may be used at the discretion of the artisan. These reporter genes are described, e.g., in K. Weising et al., Ann. Rev. Genetics, 22:421, 1988.

Several techniques exist for introducing foreign genes into plant cells, and for obtaining plants that stably maintain and express the introduced gene. Such techniques include acceleration of genetic material on coated particles directly into cells (U.S. Pat. No. 4,945,050). Plant can also be transformed using Agrobacterium technology (U.S. Pat. Nos. 5,177,010, 5,104,310, 5,149,645, 5,469,976, 5,464,763, 4,940,838, 4,693,976, 5,591,616, 5,231,019, 5,463,174, 4,762,785, 5,004,863, and 5,159,135; and European Patent Applications 116718, 290799, 320500, 604662, 627752, 0267159, and 0292435). Other transformation technologies include whiskers technology (see U.S. Pat. Nos. 5,302,523 and 5,464,765). Electroporation technology has also been used to transform plants (see WO 87/06614, WO 92/09696 and WO 93/21335, and U.S. Pat. Nos. 5,472,869 and 5,384,253). Viral vector expression systems can also be used, such as those described in U.S. Pat. Nos. 5,316,931, 5,589,367, 5,811,653, and 5,866,785. Other techniques include microinjection, the ultrasonic method, polyethylene glycol-mediated protoplast transformation, the poly-L ornithine method, and calcium phosphate precipitation.

An exemplary method for the introduction of nucleic acids into plant cells uses the principle of the binary vector system (Hoekema et al., Nature 303:179, 1983; and European Patent Application No. 0120516). This method uses Agrobacterium strains containing a vir plasmid having a virulence gene and a compatible plasmid with the gene construct to be transferred. The binary vectors contain between the left- and right-border sequences of the T-DNA, an Hph gene coding for hygromycin resistance, and a multiple cloning site to clone in the required gene constructs. Agrobacterium cells containing the binary vector are co-cultivated with tissues CT cultured cells from desired plant species. The transformed plant cells are selected by nutrient media containing antibiotics or chemicals and induced to regenerate differentiated plants on such media. The resulting plants contain and express the DNA construct constitutively or at the germination, sprout, or seedling stage.

In addition to numerous technologies for transforming plants, the type of tissue that is contacted with the gene s of interest may vary as well. Suitable tissue includes, but is not limited to, embryogenic tissue, callus tissue, hypocotyl, meristem, and the like. Almost all plant tissues may be transformed during dedifferentiation using the appropriate techniques described herein.

Regardless of the transformation system used, a gene containing a promoter of the invention can be incorporated into a gene transfer vector adapted to express the gene in a plant cell by including in the vector an expression control sequence (plant promoter regulatory element) other than a promoter of the invention. The vector can, however, contain various other genes besides the one driven by a promoter of the invention. For these other genes included in the vector, genetic regulatory elements from a variety of sources (e.g., microbial, plant, or animal sources) can be used efficiently in plant cells to express foreign genes. For example, promoter regulatory elements of bacterial origin, such as the octopine synthase promoter, the nopaline synthase promoter, the mannopine synthase promoter may be used. Promoters of viral origin, such as the cauliflower mosaic virus (35S and 19S) are also desirable. Plant promoter regulatory elements also include, but are not limited to, ribulose-1,6-bisphosphate carboxaylase small subunit promoter, beta-conglycinin promoter, phaseolin promoter, ADH promoter, heat-shock promoters, and tissue specific promoters and the like. Numerous promoters are available to skilled artisans for use at their discretion. Other promoters that can be used to direct expression of a protein, in conjunction with expression directed by a promoter of the invention, include embryo-specific, sprout-specific, seedling-specific, constitutive, inducible, or growth stage-specific promoters.

The nucleic acids of the invention can also include enhancer sequences, such as those found in the rice αAmy3 promoter (Lu et al., J. Biol. Chem. 273:10120–10131, 1998), the CaMV 35S promoter (Kay et al., Science 236:1299–1302, 1987), and the 3'untranslated region of αAmy3 (Chan et al., Plant J. 15:685–696, 1998; and Chan et al., Proc. Natl. Acad. Sci. USA 95:6543–6547, 1998).

Other regulatory sequences include a DNA sequence encoding a signal peptide for directing the recombinant protein toward the endoplasmic reticulum, vacuole, protein body, or extracellular space. A suitable signal peptide is that of αAmy8 (Chan et al., J. Biol. Chem 269:17635–17641, 1994), the sequence encoding for which can be fused upstream of the DNA sequence encoding the recombinant protein. Other regulatory sequences include terminator sequences and polyadenylation signals, e.g., the 3'untranslated region of the Nos gene of *A. tumefaciens* or a rice αamylase gene.

The transgenic organs of the invention, including germinating embryos, sprouts, and seedlings, can produce high levels of recombinant protein and can be applied to a variety of industrial process directly, e.g., in animal feed or processed foods. Alternatively, the expressed recombinant proteins can be extracted and, if desired, purified using standard methods before its use in the manufacturing of feeds or foods.

The advantage of using transgenic germinating embryos, sprouts, or seedlings containing a promoter of the invention for recombinant production of proteins include: (1) transgenic germinating embryos and seedlings produce higher levels of recombinant proteins than at later growth stages of plant development, if a promoter of the invention is used to express the recombinant protein at an early stage of plant development; (2) the sprout, leaf, stem, and root of a transgenic seedling or embryo provide multiple host organs for production of one recombinant protein in high yield; (3) a transgene containing a promoter of the invention can be combined with another transgene for high level expression in the embryo and another early tissue, such as the endosperm (e.g., using an a-amylase gene promoter); (4) expression of a protein for human consumption or use in plant tissues avoids contamination of downstream products by animal pathogens and microbial toxins; (5) transgenic seeds capable of producing a recombinant protein in situ are suitable for long-distance transportation and long-term storage; (6) after arrival of the transgenic seed at its destination, a high yield of embryo, sprout, or seedling biomass can be obtained by germination and cultivation of the seeds in a short period of time using controlled condition and a suitable facility; and (7) production costs can be reduced because the recombinant protein factory (i.e., the seed or embryo) is contained within a small volume and does not require sophisticated environmental conditions for viability.

Without further elaboration, it is believed that one skilled in the art can, based on the above disclosure, the isolation of the OsGRP-A1 promoter, and the production of transgenic seeds as shown below, utilize the present invention to its fullest extent. The following example is to be construed as merely illustrative of how one skilled in the art can isolate and use the promoters of the invention, and are not limitative of the remainder of the disclosure in any way. Any publications cited in this disclosure are hereby incorporated by reference.

Materials and Methods

Plant Material. The rice variety used in this study was *Oryza sativa* L. cv. Tainung 67. Immature seeds were dehulled, sterilized with 2.4% NaOCl for 1 hour, washed extensively with sterile water, and placed on N6D agar medium (Toki, Plant Mol. Biol. Rep. 15:16–21, 1997) for callus induction. After one month, callus derived from scutella was subcultured in fresh N6D medium for transformation, or in a liquid MS medium (Murashige et al., Physiol. Plant 15:473–497, 1962) containing 3% sucrose and 10 mM 2,4-D to establish a suspension cell culture, as previously described (Yu et al., J. Biol. Chem. 266:21131–21137, 1991).

Screening of cDNA and genomic DNA libraries. Rice suspension cells were cultured in sucrose-containing medium for 5 days and transferred to sucrose-containing (+S) or sucrose-free (−S) medium for 4 hours. Cells were collected and total RNA was purified. Poly(A)$^+$ RNA was further purified using an oligo (dT) cellulose spin column (5 Prime to 3 Prime). The poly(A)$^+$ RNA isolated from −S cells was used to construct a cDNA library in the lambda GEM-2 vector (Promega). The $^{32}$P-labeled single-stranded cDNA probe was prepared from poly(A)$^+$ RNA of +S or −S cells using an oligo(dT) primer and AMV reverse transcriptase. Duplicated filter lifts from high density platings of the cDNA library were then differentially screened with the cDNA probes. The phage plaques that hybridized strongly with the cDNA probes of both +S and −S cells were isolated. One of the isolated clones with an insert of 0.6 kb in length was sequenced and found to be highly homologous to plant glycine-rich RNA-binding proteins. This clone was then used to screen a rice genomic DNA library (Clontech). One positive clone containing a 3.5 kb DNA insert was obtained, designated as OsGRP-A1, and subcloned into the HindIII site of pBluescript (Stratagene) to generate pBS-A1.

Primer extension analysis. 5'-Primer extension analysis was performed as described in Sambrook et al., *Molecular Cloning: A Laboratory Manual*, 2nd ed., Cold Spring Harbor Laboratory, Cold Spring Harbor, N.Y., 1989. Total RNA was isolated from germinating embryos 3 days after germination. Poly(A)$^+$ RNA was purified from the total RNA and hybridized with $^{32}$P-labeled primer P2 (5'-CTCAACCCACTAAACCC-3'; SEQ ID NO:8), which is complementary to the sequence immediately upstream of the start codon in OsGRP-A1. The polymerization reaction was conducted with SUPERSCRIPT®) reverse transcriptase (GIBCO BRL). Dideoxynucleotide sequencing of pBS-A1 was also performed using the P2 primer and served as the sequence reference. The extension product and the sequence reference were electrophoresed and visualized by autoradiography.

Plasmid construction. Plasmid pRY18 carried a 3.8-kb DNA fragment containing a rice genomic rDNA cluter, the 3' half portion of the 17S rRNA gene, the complete 5.8 S rRNA gene, and the 5' half portion of the 25S rRNA gene in pUC13 (Sano et al., Genome 33:209–218, 1990). A 1.8 kb DNA fragment containing the 5' flanking region of OsGRP-A1 was PCR-amplified using pBS-A1 as template, the T7 primer (Stratagene), and the primer 5'-GATATCTGCAGCTCAACCCACTAAACC-3' (SEQ ID NO:9), which contains almost all of the sequence of primer P2 but is longer to accommodate a restriction site. This DNA fragment was cleaved with PstI and HindIII and cloned into the same sites in pBX-2 (Ho et al., Plant Physiol. 122:57–66, 2000), producing a transcriptional fusion with the gusA (Jefferson et al., Plant Mol. Biol. Rep. 5:387–405, 1987) coding region and the Nos terminator. The OsGRP-A1-gusA-Nos chimeric gene was excised from pBX-2 with HindIII and inserted into the HindIII site of pSMY1H (Ho et al., supra) to generate pOsGRP-A1-GUS.

The 5'untranslated region of OsGRP-A1 was PCR-amplified using pBS-A1 as template and oligonucleotides P1 (5'-CGTGCTCTCTTTGAGGT-3' [SEQ ID NO:10]) and P2 as primers. The 96 bp PCR product was designated A1S and used as a gene-specific probe in the genomic DNA and RNA gel blot analyses described herein.

Genomic DNA gel blot analysis. Genomic DNA was isolated from rice calli as described in Sheu et al., J. Biol. Chem. 271:26998–27004, 1996. Ten milligrams of genomic DNA was digested with restriction enzymes, fractionated in 0.8% agarose gel, and transferred to a nylon membrane (MSI). Hybridization was performed at 42° C. using $^{32}$P-labeled OsGRP-A1 cDNA random primer or gene-specific DNA (A1S) as a probe.

RNA gel blot analysis. Total RNA was isolated from various tissues of germinating seeds or plants as described in Yu et al., J. Biol. Chem. 266:21131–21137, 1996 and isolated from cultured suspension cells using a TRIZOL® reagent (GIBCO BRL). RNA gel blot analysis was performed as described in Thomas, Plant Mol. Biol. Rep. 15:16–21, 1983. Briefly, 10 μg of total RNA were electrophoresed in a 1 % agarose gel containing 10 mM sodium phosphate buffer (pH 6.5), transferred to a nylon filter, and hybridized with $^{32}$P-labeled A1S or rDNA random primer probe. The blot was visualized using autoradiography.

Transformation. Plasmid pOsGRP-A1-GUS was introduced into *Agrobacterium tumefaciens* strain EHA101 (Hood et al., J. Bacteriol. 168:1291–1301, 1986) with an electroporator (BTX), following the manufacturer's instruction. Calli induced from immature rice seeds were co-cultured with Agrobacterium according to the methods described by Hiei et al., Plant J. 6:271–282, 1994; and Toki et al., supra.

Histochemical localization of GUS activity. The dehulled seeds were sterilized with 2.4% NaOCl and placed on two pieces of sterile Whatman No. 1 filter paper in a petri dish. Sterile water was applied to the filter paper to imbibe the seeds. The seeds were incubated at 28° C. in darkness for various time periods. After incubation, germinating seeds and seedlings were stained with 1 mM 5-bromo-4-chloro-3-indolyl β-D-glucuronide (X-gluc) at 37° C. in darkness for 12 hours and photographed.

Results

Cloning and characterization of OsGRP-A1. The OsGRP-A1 genomic clone containing the 3.5 kb insert was sequenced. Comparison of the OsGRP-A1 sequence with sequence data in GenBank indicated that the coding sequence of OsGRP-A1 shares significant homology (98% amino acid identity) with that of another rice glycine-rich RNA-binding protein (GenBank Accession No. AF010579). The transcription start site was mapped to a cytosine nucleotide 96 bp upstream from the translation initiation codon and designated as +1. A typical TATA box is located at about position −37 from the transcription start site. The protein sequence deduced from the cDNA revealed that the protein contains a consensus RNA-binding, domain (CS-RBD) (Kenan et al., Trends Biochem Sci 16:214–220, 1991). CS-RBD includes a highly conserved octamer sequence or ribonucleoprotein consensus sequence (RNP-CS or RNP-1) near the middle of the domain and a less well conserved hexamer sequence (RNP-2) towards the N-terminus of the domain. The C-terminus of OsGRP-A1 consists mainly of repeating glycine residues interspersed with tyrosine and arginine.

OsGRP-A1 is a member of a gene family. DNA gel blot analysis was performed to determine the copy number of genes encoding glycine-rich RNA-binding proteins in the rice genome. By using OsGRP-A1 cDNA as a probe, under very high hybridization stringency, two strong hybridization bands with similar molecular weights and some minor bands were observed in BamHI or HindIII digests of rice genomic DNA, and several hybridization bands with similar intensity w ere observed in EcoRI digests. This finding suggests that the rice glycine-rich RNA-binding proteins are encoded by a multigene family. By using gene-specific DNA A1S as a probe, only a single band was hybridized.

OsGRP-A1 is constitutively expressed in rice suspension cells cultured under various stress conditions. It was known that expression of plant glycine-rich RNA-binding proteins is induced in response to various stresses, including ABA (Gomez et al., Nature 334:262–264, 1988), water and chemical stress (Didieijean et al., Plant Mol. Biol. 18:847–849, 1992), wounding (Sturm, Plant Physiol. 99:1689–1692, 1992), and cold (Horvath et al., Plant Mol. Biol. 38:531–538, 1998). To determine whether expression of OsGRP-A1 in cultured rice suspension cells is regulated by stress, cells were cultured in medium lacking sucrose or in as medium containing sucrose plus NaCl, mannitol, or ABA for various lengths of time. Total RNA was purified and subjected to RNA gel blot analysis using A1S as a probe. Levels of OsGRP-A1 mRNA were similar in cells under various stress conditions for various lengths of time, except that the mRNA level was slightly reduced 16 hours after sucrose starvation. These results suggest that OsGRP-A1 is constitutively expressed in rice suspension cells for at least 16 hours regardless of whether cells were stressed or not.

OsGRP-A1 is highly expressed in the embryos of germinating rice seeds and rice seedlings. To examine the expression pattern of OsGRP-A1 in germinating seed and seedling, total RNA was purified from embryos and endosperms within 10 days after germination and subjected to gel blot analysis using A1S as a probe. OsGRP-A1 mRNA was barely detectable in the embryo of dry seeds, became detectable 1 hours after imbibition, and then gradually increased with incubation time. The levels of OsGRP-A1 mRNA in the embryos of germinating seed and seedling were similar within the 10-day period after germination. Additionally, the levels of OsGRP-A1 in the embryos were significantly higher than that in endosperm.

OsGRP-A1 is highly expressed in the shoots of rice seedlings but lowly expressed in various tissues of young and old rice plants. To compare the expression pattern of OsGRP-A1 in plants of various ages, total RNA was purified from various tissues of rice at different growth stages and subjected to gel blot analysis using A1 S as a probe. OsGRP-A1 mRNA levels were high in the shoots of rice seedlings within 10 days after germination, but substantially decreased 20 days after germination. OsGRP-A1 mRNA levels were barely detectable in the roots of 20 day-old seedlings and all tissues of 3 month-old mature plants. The above results thus indicate that the expression of OsGRP-A1 in the vegetative tissues of rice is developmentally and spatially regulated.

OsGRP-A1 promoter activity is high in the germinating embryos and seedlings of transgenic rice. To investigate the use of the OsGRP-A1 promoter for expression in germinating seeds and seedlings, a 1.8 kb DNA fragment containing the 5' regulatory sequence of OsGRP-A1 was fused at the 5' end of the gusA gene. The chimeric gene was inserted into a binary vector to generate pOsGRP-A1-GUS. pOsGRP-A1-GUS was introduced into Agrobacterium for rice transformation. Transgenic rice plants were obtained and seeds were harvested. The GUS assay also indicated that GUS activity first appeared in the embryos of germinating seeds, then expanded to the shoots and roots of seedlings. Thereafter, GUS was expressed mainly in the young leaves of the seedlings. In seedlings, GUS activity was much higher in the shoots and leaves than in the roots, indicating that the OsGRP-A1 promoter is especially suitable for expression in the shoot tissues of a seedling.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid comprising SEQ ID NO:1.

2. The nucleic acid of claim 1, further comprising a heterologous sequence, wherein a portion of the nucleic acid within SEQ ID NO:1 directs transcription of the heterologous sequence.

3. An isolated nucleic acid comprising SEQ ID NO:2.

4. An isolated nucleic acid comprising a promoter that hybridizes under stringent conditions to a nucleic acid consisting of SEQ ID NO:1.

5. The nucleic acid of claim 4, further comprising a heterologous sequence, wherein the promoter directs transcription of the heterologous sequence.

6. The nucleic acid of claim 5, wherein the heterologous sequence encodes a polypeptide.

7. An isolated nucleic acid comprising a promoter that is at least 70% identical to SEQ ID NO:1.

8. The nucleic acid of claim 7, further comprising a heterologous sequence, wherein the promoter directs transcription of the heterologous sequence.

9. The nucleic acid of claim 8, wherein the heterologous sequence encodes a polypeptide.

10. The nucleic acid of claim 7, wherein the promoter is at least 90% identical to SEQ ID NO:1.

11. A vector comprising the nucleic acid of claim 1.

12. A vector comprising the nucleic acid of claim 4.

13. A vector comprising the nucleic acid of claim 7.

14. A transform ed cell comprising the nucleic acid of claim 1.

15. A transformed cell comprising the nucleic acid of claim 4.

16. A transformed cell comprising the nucleic acid of claim 7.

17. A transgenic, plant whose genomic DNA comprises the nucleic acid of claim 2.

18. The transgenic plant of claim 17, wherein the plant is a rice plant.

19. A transgenic plant whose genomic DNA comprises the nucleic acid of claim 5.

20. The transgenic plant of claim 19, wherein the plant is a rice plant.

21. A transgenic plant whose genomic DNA comprises the nucleic acid of claim 8.

22. The transgenic plant of claim 21, wherein the plant is a rice plant.

23. A transgenic seed harvested from the transgenic plant of claim 17.

24. A transgenic seed harvested from the transgenic plant of claim 19.

25. A transgenic seed harvested from the transgenic plant of claim 21.

26. A nucleic acid comprising SEQ ID NO:5 or a fragment of SEQ ID NO:5, wherein the fragment is at least 100 nucleotides in length.

* * * * *